(12) United States Patent
Singhatat

(10) Patent No.: US 6,716,224 B2
(45) Date of Patent: Apr. 6, 2004

(54) INTRACORPOREAL KNOT TIER

(75) Inventor: Wamis Singhatat, Clearwater, FL (US)

(73) Assignee: Linvatec Corporation, Largo, FL (US)

( * ) Notice: Subject to any disclaimer, the term of this patent is extended or adjusted under 35 U.S.C. 154(b) by 0 days.

(21) Appl. No.: 09/934,920

(22) Filed: Aug. 22, 2001

(65) Prior Publication Data

US 2002/0049458 A1 Apr. 25, 2002

Related U.S. Application Data

(60) Provisional application No. 60/228,304, filed on Aug. 28, 2000.

(51) Int. Cl.[7] .............................................. A61B 17/04
(52) U.S. Cl. ......................... 606/148; 289/17; 606/144
(58) Field of Search ................. 606/148, 150, 606/139, 144, 210, 211, 205, 207; 289/1.5, 17

(56) References Cited

U.S. PATENT DOCUMENTS

| | | |
|---|---|---|
| 1,625,602 A | 4/1927 | Gould et al. |
| 1,855,546 A | 4/1932 | File |
| 2,316,297 A | 4/1943 | Southerland et al. |
| 2,595,086 A | 4/1952 | Larzelere |
| 4,602,635 A | 7/1986 | Mulhollan et al. |
| 4,641,652 A | 2/1987 | Hutterer et al. |
| 4,961,741 A | 10/1990 | Hayhurst |
| 5,059,201 A | 10/1991 | Asnis |
| 5,084,058 A | 1/1992 | Li |
| 5,129,912 A | 7/1992 | Noda et al. |
| 5,176,691 A | 1/1993 | Pierce |
| 5,192,287 A | 3/1993 | Fournier et al. |
| 5,217,470 A | 6/1993 | Weston |
| 5,217,471 A | 6/1993 | Burkhart |
| 5,234,443 A | 8/1993 | Phan et al. |
| 5,234,444 A | 8/1993 | Christoudias |
| 5,234,445 A | 8/1993 | Walker et al. |
| 5,250,054 A | 10/1993 | Li |
| 5,250,055 A | 10/1993 | Moore et al. |
| 5,261,917 A | 11/1993 | Hasson et al. |
| 5,269,791 A | 12/1993 | Mayzels et al. |
| 5,281,236 A | 1/1994 | Bagnato et al. |
| 5,282,809 A | 2/1994 | Kammerer et al. |
| 5,284,485 A | 2/1994 | Kammerer et al. |
| 5,324,298 A * | 6/1994 | Phillips et al. ............... 606/148 |
| 5,391,175 A | 2/1995 | Sharpe et al. |
| 5,391,176 A | 2/1995 | de la Torre |
| 5,397,326 A | 3/1995 | Mangum |
| 5,403,330 A | 4/1995 | Tuason |
| D359,355 S | 6/1995 | Ferragamo et al. |
| 5,423,836 A | 6/1995 | Brown |
| 5,423,837 A | 6/1995 | Mericle et al. |
| 5,437,682 A | 8/1995 | Grice et al. |
| 5,439,467 A | 8/1995 | Benderev et al. |
| 5,439,470 A | 8/1995 | Li |

(List continued on next page.)

OTHER PUBLICATIONS

Super Revo Rotator Cuff Repair Surgical Technique, The Ideal Fixation Device for Rotator Cuff Repair, Linvatec Brochure CST 3018 2001, 2003 Rev 1 4/03.

*Primary Examiner*—Michael J. Milano
*Assistant Examiner*—Bradford C Pantuck
(74) *Attorney, Agent, or Firm*—Gene Warzecha

(57) ABSTRACT

An instrument and method for tying two suture ends into a knot. A tubular outer member is provided with a transverse slot for capturing a length of one of the suture ends therein. A slidable inner member has a pair of diametrically opposed, suture engaging fingers for pushing the captured suture from the tubular member and for rotating it to form a loop between the fingers. The other suture end is passed through the loop to create a knot. The instrument is then repositioned and used as a knot pusher so the knot may be tightened and properly positioned. Successive use of the instrument to create successive loops and knots ultimately results in a final knot securing the suture ends.

15 Claims, 7 Drawing Sheets

U.S. PATENT DOCUMENTS

| | | |
|---|---|---|
| 5,462,560 A | 10/1995 | Stevens |
| 5,501,690 A | 3/1996 | Measamer et al. |
| D368,776 S | 4/1996 | Toy et al. |
| 5,653,719 A | 8/1997 | Raiken |
| D386,583 S | 11/1997 | Ferragamo et al. |
| D387,161 S | 12/1997 | Ferragamo et al. |
| 5,769,862 A * | 6/1998 | Kammerer et al. .......... 606/148 |
| 5,816,258 A * | 10/1998 | Jervis ......................... 128/898 |
| 5,860,990 A * | 1/1999 | Nobles et al. ............... 606/144 |
| 6,074,395 A | 6/2000 | Trott et al. |
| 6,221,084 B1 * | 4/2001 | Fleenor ....................... 606/148 |

* cited by examiner

INTRACORPOREAL KNOT TIER

This application claims the benefit of provisional application No. 60/228,304 filed Aug. 28, 2000.

BACKGROUND OF THE INVENTION

1. Field of the Invention

This invention relates to surgical knot tying devices. In particular, the invention relates to knot tying devices suitable for forming knots in suture during endoscopic, e.g. arthroscopic, surgical procedures.

2. Description of the Prior Art

Repairing tissue during endoscopic surgical procedures often requires suturing the tissue. The suture is sometimes used alone to stitch together tears or reattach soft tissue to bone, etc., and sometimes used with anchors to tie tissue to a supporting surface. The suture is generally secured by tying the ends or legs in a knot which may be formed in a variety of styles and in a variety of ways. Clearly, knot tying in endoscopic procedures is more challenging than in open procedures because of the difficulty in manipulating suture legs in small spaces. Consequently, numerous devices have been developed to assist a surgeon.

Knots may be formed within the body (intracorporeally) or outside the body (extracorporeally). In either case, the formation of the knot requires significant manual manipulation of the suture legs to be tied. In the case of extracorporeal knots, the manipulation is somewhat easier, but once a knot or a portion of a knot is formed it must be pushed down to tighten the suture against the tissue. Simple knot pushers are available for this purpose as exemplified by U.S. Pat. Des. 359,355; Des. 386,583 and Des. 387,161 (all to Ferragamo et al.) and U.S. Pat. No. 2,595,086 (Larzelere), U.S. Pat. No. 4,602,635 (Mulhollan et al.), incorporated by reference herein.

Tightening a double or multiple knots which are initially formed extracorporeally and then pushed to the tissue site is shown in U.S. Pat. No. 4,961,741 (Hayhurst) and 5,084,058 (Li) as being accomplished by a relatively complex device which requires the suture legs to be threaded through the device to pre-form loose knots to be pushed. Another device known for this purpose utilizes a knot holding forceps and a cooperating knot pusher to tighten double or multiple knots as shown in U.S. Pat. No. 5,217,471 (Burkhart).

Intracorporeal knot formation is often accomplished simply with manual manipulation of suture within the workspace available through the use of forceps, graspers, snares and the like. Some instruments are known to assist in this manipulation by forming one of the suture legs into loops or twisting the legs together. For example, cannulated corkscrew devices facilitate such knot formation as exemplified by U.S. Pat. No. 4,641,652 (Hutterer et al.). Knot pushers may be used in these cases as well.

There is a continuing need to improve endoscopic knot formation to simplify the process. It is accordingly an object of this invention to provide an intracorporeal knot tier which can manipulate suture to facilitate the formation of knots at a work site.

It is another object of this invention to provide an intracorporeal knot tier by which a user can with one hand form a loop in a length of suture and then form a knot by passing through the loop the other end of the suture.

DESCRIPTION OF THE PREFERRED EMBODIMENT

Figure 1:
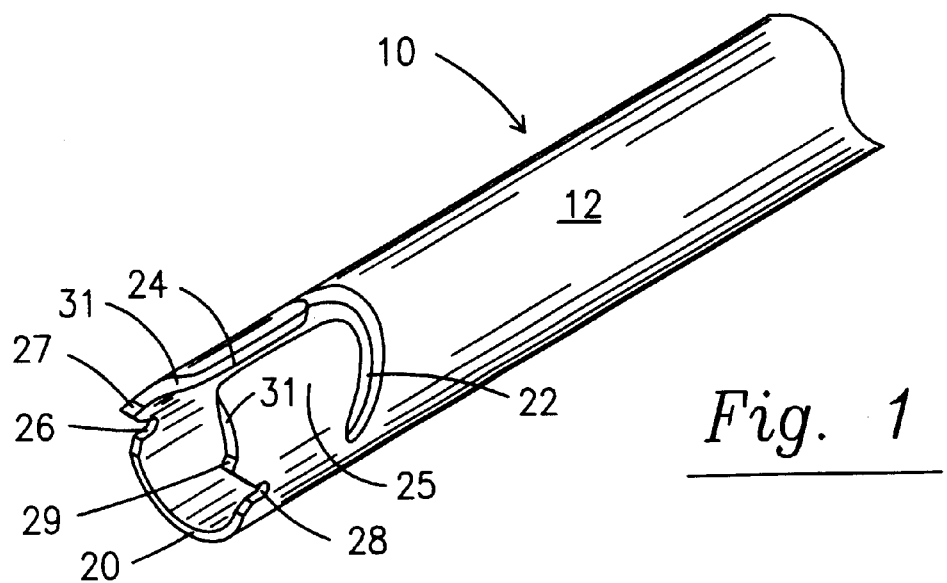
FIG. 1 is a front perspective view of the distal end of a knot tier constructed in accordance with the principles of this invention.
Figure 2:
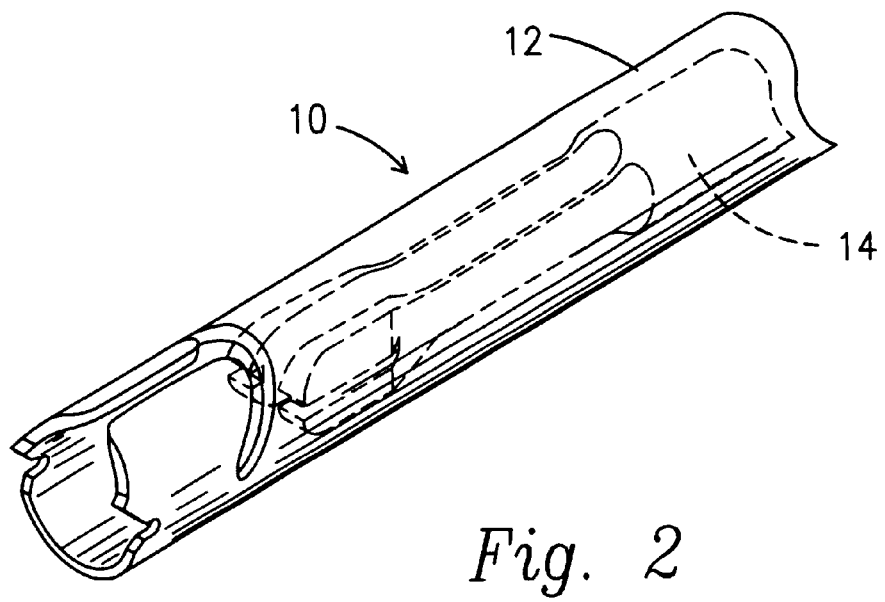
FIG. 2 is a partially cut-away view of FIG. 1 showing the internal structure of the knot tier.

As shown in FIGS. 1 and 2, knot tier 10, constructed in accordance with the principles of this invention, comprises an outer tubular member or housing 12 and an inner cylindrical manipulating member 14 slidably situated within tubular member 12. The term "knot tier" is used to describe the invention because it is capable of forming a knot and then pushing it into place. As such, the invention is a knot former and knot pusher, thus combining functions that in many prior art devices are accomplished with separate instruments. The terms "tie" and "tying" as used herein mean the formation of loops and the passage of suture through such loops to form a knot. These terms encompass the formation of loose knots before they are cinched or pushed into place against the tissue to be sutured. Instrument 10 is elongated and narrow in order to enable it to be used during endoscopic surgical procedures and, while only the distal end of the instrument is shown in the drawings, it will be understood that the proximal end comprises an appropriate handle and/or other structures designed to manipulate the distal end of the instrument as will be better understood below.

Figure 12:
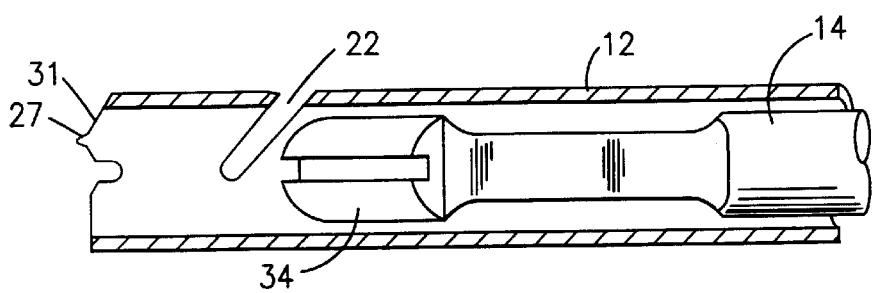
FIG. 12 is a side elevation view, in cross-section, of FIG. 4.
Figure 13:
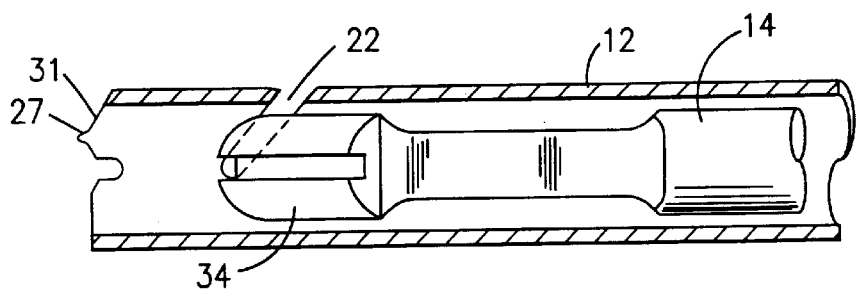
FIG. 13 is a side elevation view, in cross-section, of FIG. 5.

Tubular member 12 has a distal end 20 which comprises a transverse slot 22 for engaging suture (hereafter called "captured suture") and positioning it transversely within the interior to tubular member 12 for engagement with cylindrical member 14 as will be understood below. Distal end 20 includes a longitudinally aligned slot 24 in its cylindrical wall 25 in order to enable the knot tier to push the knot after it has been formed. Slot 24 works in conjunction with a pair of diametrically opposed, distally facing notches 26 and 28 designed to engage and tighten knots created by instrument 10. As will be understood below, when knot tier 10 is used as a knot pusher only one notch 26 or 28 will be used depending upon whether right or left handed operation of the instrument is selected. Distal end 20 also includes diametrically opposed projections or points 27 and 29 designed to facilitate separating two adjacent suture strands. Very often two or more suture legs emanate from the point of attachment (e.g. suture anchor) in a way which causes them to be contiguous and parallel. Points 27 and 29 may be pushed between adjacent suture legs to separate them. As best seen in FIG. 12, points 27 and 29 are adjacent an inclined surface 31 extending proximally to further separate adjacent suture legs and to facilitate guiding one of the suture legs toward slot 22.

Figure 3:
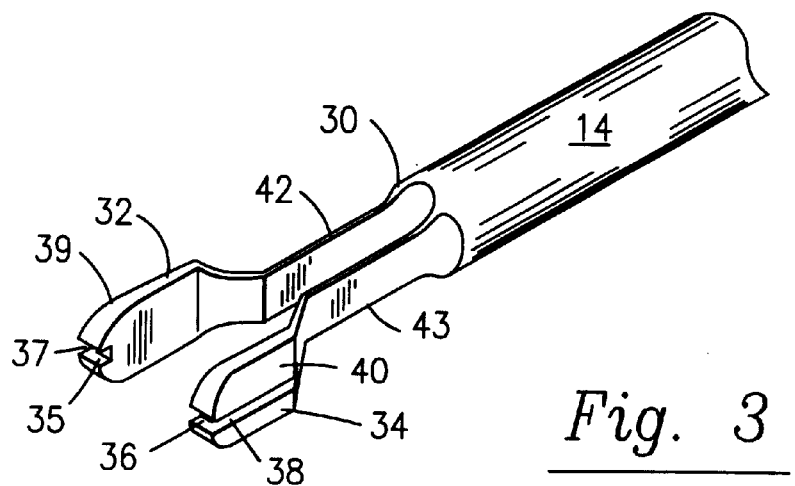
FIG. 3 is a front perspective view of an internal component (shown in FIG. 2) in an expanded state.

Referring to FIGS. 2 and 3, inner cylindrical member 14 has at its distal end 30 a pair of diametrically opposed finger members 32 and 34 for engaging and manipulating suture as will be understood below. The finger members are spaced apart to enable them to engage the captured suture at spaced apart points to facilitate the formation of a loop. As will be understood below, successive activation of the finger members creates successive loops and interim knots which ultimately create the final knot desired at the work site. Finger members 32 and 34 are sufficiently resilient and biased radially outwardly to enable them to both conform to the cylindrical surface interior of tubular member 12, as best in FIG. 2, and to expand when in an extended position, as shown in FIG. 3. Fingers 32 and 34 are provided with distally facing suture receiving channels 35 and 36, respectively, and longitudinally extending suture receiving channels 37 and 38, respectively. Channels 37 and 38 are formed in arcuate surfaces 39 and 40, respectively, which conform to the interior cylindrical surface of outer member 12 and are deep enough to receive suture therein to minimize its frictional contact with such inner surface. Finger members 32 and 34 are situated at the distal ends of support members 42 and 43, respectively, which are smaller than and situated radially inwardly of slot 22 in order to avoid interference with suture captured in the slot.

Figure 4:
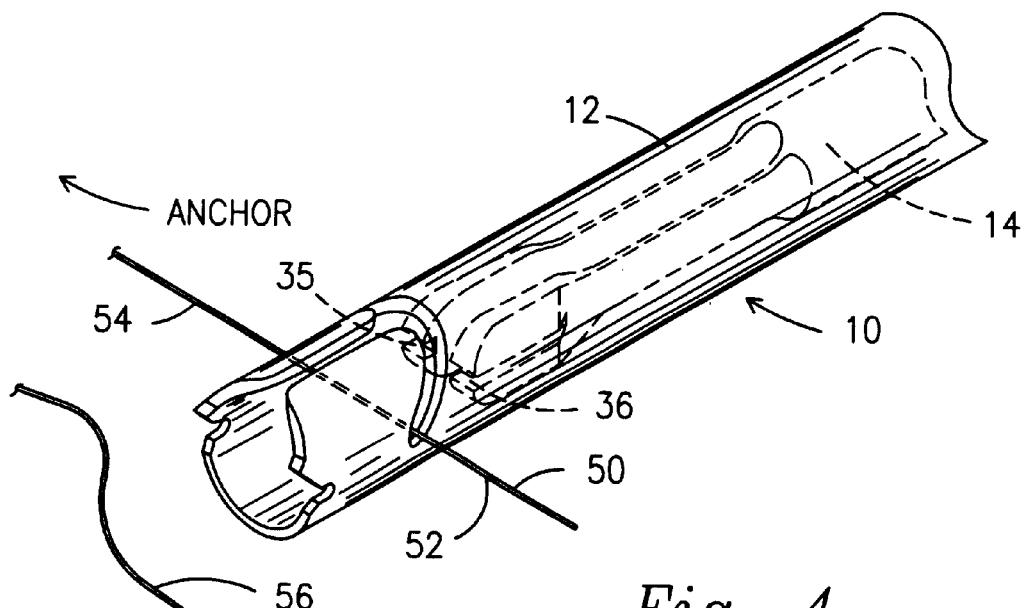
FIG. 4 is a view of FIG. 2 showing a step in the process of using the knot tier.
Figure 5:
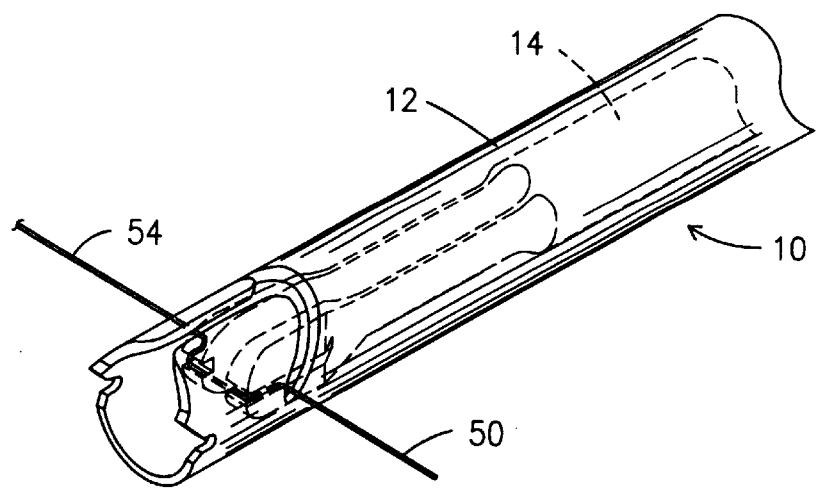
FIGS. 5 through 11 are sequential views of FIG. 4 showing the subsequent steps in the process of using the knot tier.
Figure 6:
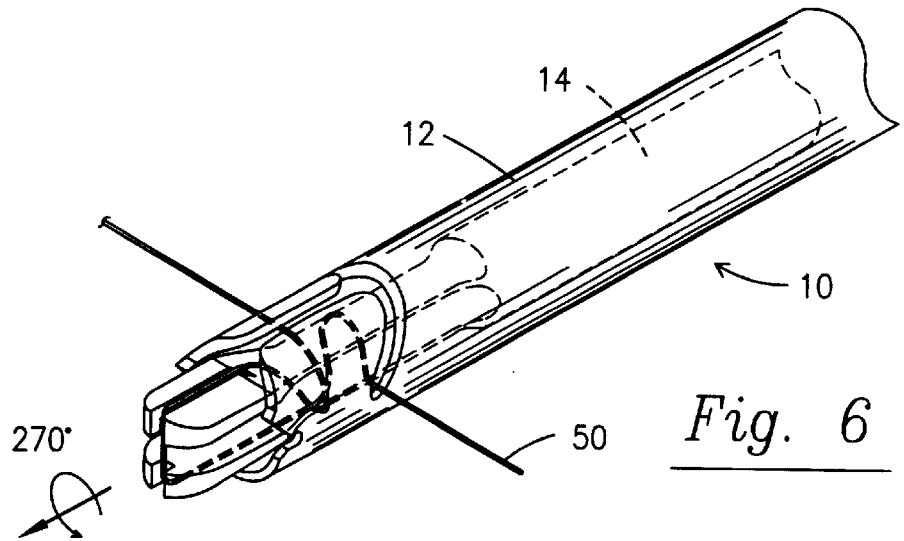
Figure 11:
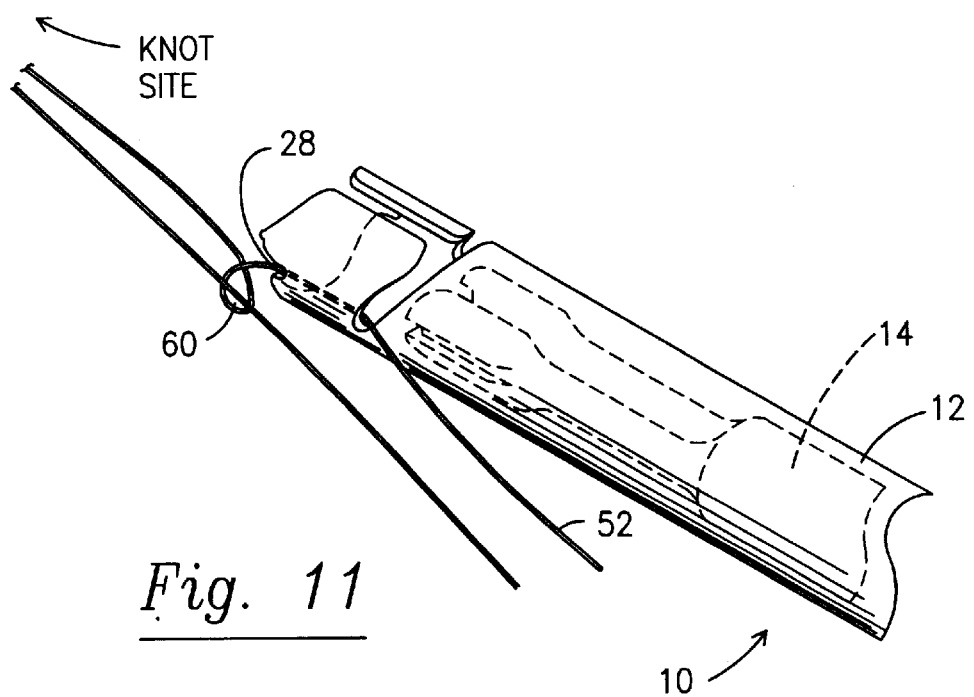

The intracorporeal knot forming operation of instrument 10 will best be understood by reference to FIGS. 4 through 9. As shown in FIG. 4, with inner member 14 at its proximal-most position, or least proximal to slot 22, instrument 10 is manipulated so that suture 50 having a proximal portion 52 and a distal portion 54 is received and seated within slot 22 (FIG. 4). Suture 50 is one leg of a suture extending from an anchor or other location where a knot is to be formed, the other leg being identified by the numeral 56. Legs 50 and 56 could be one continuous length of suture or they could be two separate pieces with one end of each anchored at a work site by a suture anchor, for example. The suture is, when seated in slot 22, positioned distally of inner member 14 in alignment with transverse suture receiving channels 35 and 36. As shown in FIG. 5, inner member 14 is moved distally by a handle or other structure at the proximal end of the instrument (not shown) and begins to push the suture 50 from the interior of outer member 12. In the preferred embodiment, as inner member 14 is further moved distally it is, as shown in FIG. 6, simultaneously rotated 270° counterclockwise (as viewed from the distal end of instrument 10). The direction of rotation creates an overhand half-hitch knot as best seen in FIG. 11. The rotation may be effected by a cam (not shown) on one component (member 12 or 14) riding in a helical cam track (not shown) on the other component, or other suitable means. The distal linear motion of member 14 could be separate from the rotation, although in the preferred embodiment these motions are simultaneous.

Figure 7:
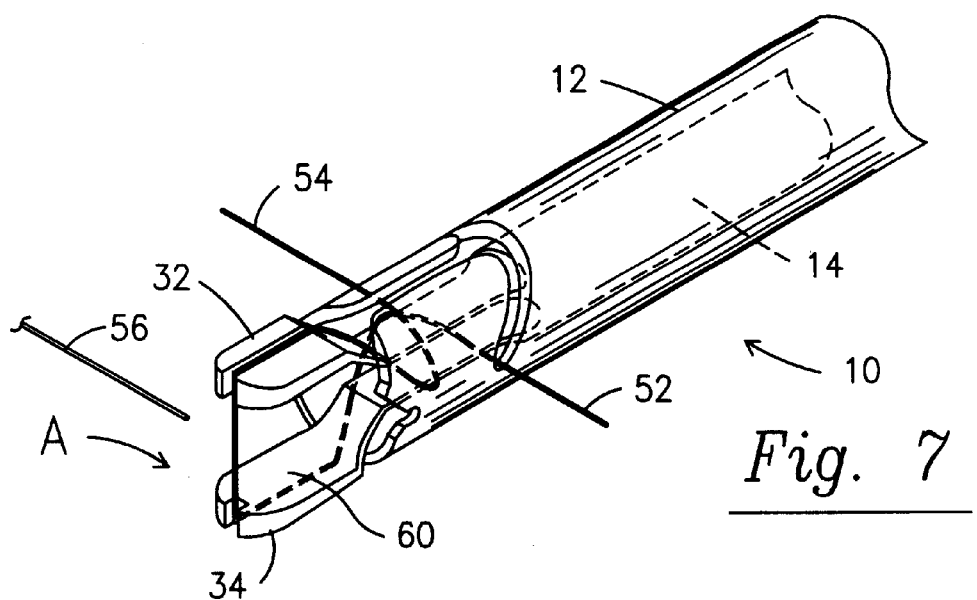
Figure 8:
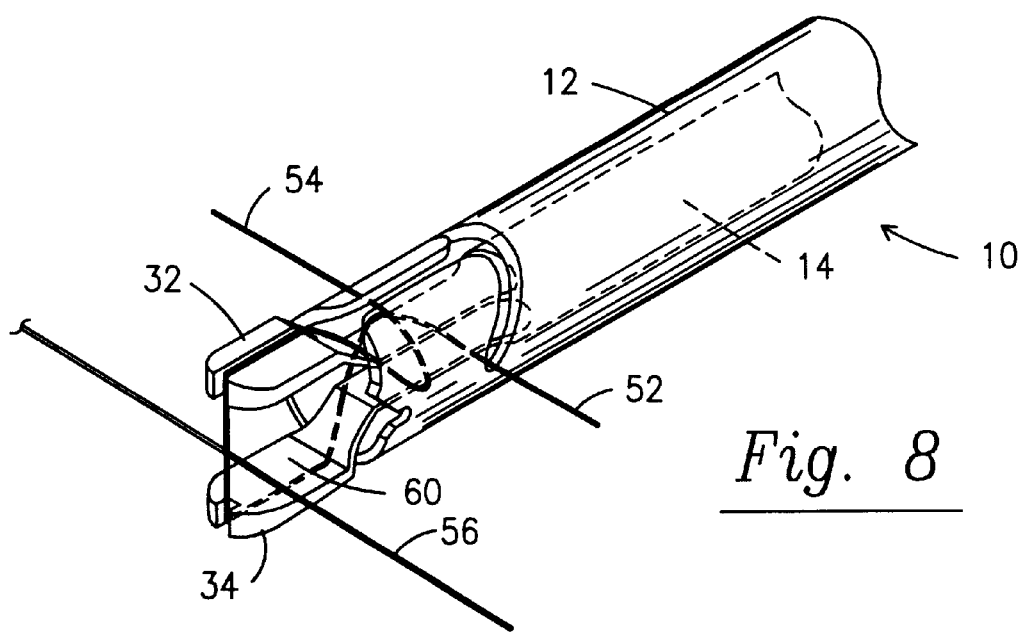
Figure 9:
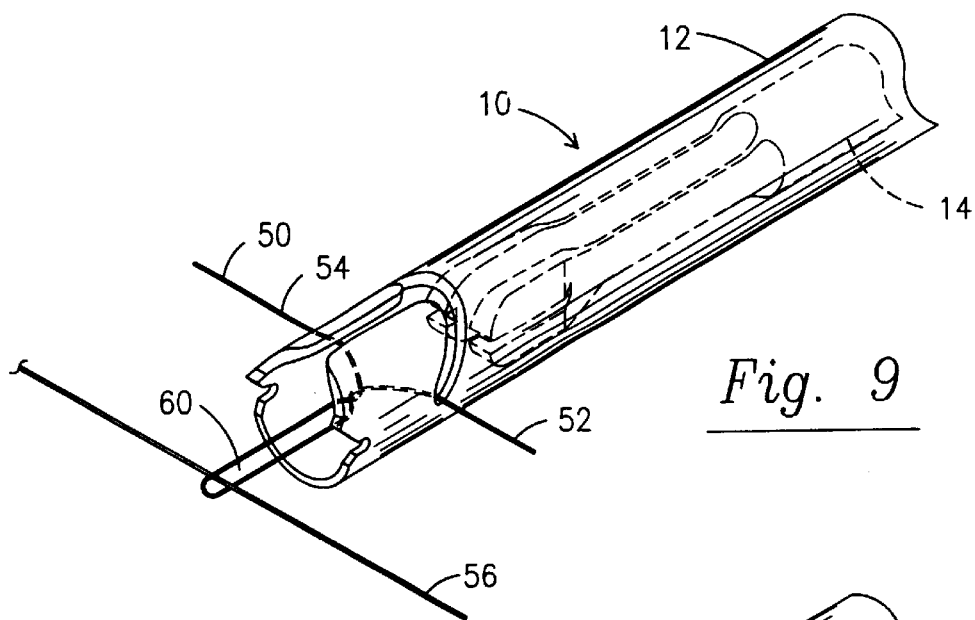

As fingers 32 and 34 clear the end 20 of the outer tube 12 their natural bias will expand the fingers into the position shown in FIG. 7. The spreading of fingers 32 and 34 thus creates a loop 60 within suture leg 50. The size of the loop is a function of the spread between the finger members and the length of longitudinal channels 37 and 38. Suture leg 56 is then pulled through loop 60 in the direction A by grasping it with a suture retriever, forceps, snare or other similar device to produce the configuration shown in FIG. 8. Inner member 14 is then retracted along the same path (i.e. reverse rotation), as shown in FIG. 9, thereby causing loop 60 to close upon suture leg 56 in order to form a half-hitch knot. While the preferred embodiment causes the fingers to rotate in the opposite direction upon retraction, the invention could be made to function without rotation on retraction. The absence of rotation on the retraction motion could be caused by another "cam track" or similar device.

Figure 10:
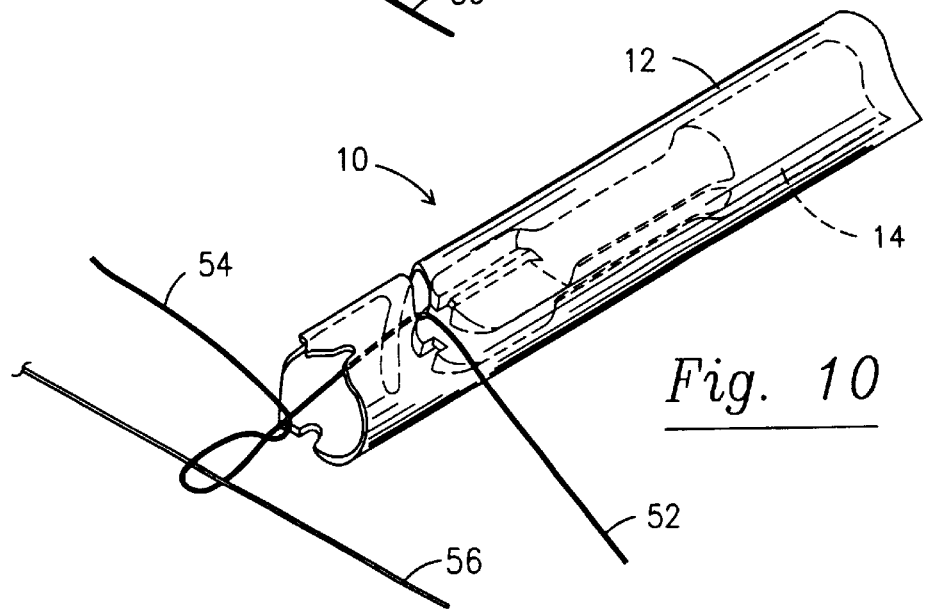

As best seen in FIG. 10, suture leg 50 may then be partially disengaged from instrument 10 by rotating outer member 12 in a predetermined direction (counterclockwise in FIG. 10) to allow the distal portion 54 of suture leg 50 to pass from a portion of slot 22 and into the interior of member 12 through longitudinal slot 24, thereby leaving suture leg 50 in the remaining portion of slot 22 and in the interior of member 12. This facilitates the next step in which instrument 10 may then be positioned for use as a knot pusher as shown in FIG. 11 in order to engage proximal suture portion 52 within notch 28 at a point immediately adjacent loop 60 in order to push the knot toward the desired knot site. It should be noted that, for purposes of disengaging suture so the instrument can be used as a knot pusher, knot tier 10 will always be rotated so as to release the distal portion of the suture in slot 22. It will also be understood that FIG. 10 shows the use of knot tier 10 in right-handed operation. For left-handed operation, the direction of rotation of knot tier 10 would be opposite to that shown in FIG. 10. More precisely, the particular notch used (26 or 28) depends upon the direction in which member 12 is rotated to disengage the distal portion of the suture leg. While right-handed and left-handed users may tend to rotate this member in opposite directions, it will be understood that both types of users could choose to rotate the member differently, provided the distal end of the suture leg is disengaged. Additional interim knots may be made as desired by repeating the preceding steps. For each loop formed, by varying the sequence of which suture leg is captured in slot 22 and the direction of rotation of member 14 used to form the loop, the knots ultimately formed will be of varying types for varying purposes depending upon surgeon preference. For example, while the first loop of the knot shown above was formed by capturing suture leg 54 and passing leg 56 through the loop, a second loop could be formed by capturing either leg 54 or 56, a third loop could be formed similarly, and so on. While the preferred embodiment is shown with an inner manipulating member which is turned 270° to form a loop, it will be understood that other embodiments could be made to form a loop after any number of degrees sufficient to form a loop for the other leg of suture to pass through. Thus, turning the inner member through 180°, 270°, 360°, 450°, 540°, etc. would enable a knot to be formed. The turns through 270° and multiples of 180° thereafter enable the loop to be oriented as shown in FIG. 7 to facilitate passage of the other suture leg through the loop. Turns through 180° and multiples of 180° thereafter would have the loop oriented in a plane perpendicular to that of the loop in FIG. 7.

As a further example, knot tier 10 may be used during an arthroscopic shoulder reconstruction procedure to form a particular type of prior art knot, commonly referred to as a Revo® knot. The method of creating a Revo® knot using knot tier 10 involves first capturing suture leg 50, forming and pushing a first interim (underhand) half-hitch knot. An underhand knot is the same as the overhand knot previously described, but is formed by rotating tubular member 14 clockwise instead of counterclockwise as shown in FIG. 6. Suture leg 50 is again captured and a second interim (underhand) half-hitch knot is then formed and pushed to the knot site. Then a third interim (overhand) half-hitch knot is formed by capturing leg 50 as shown in FIGS. 4–10 and pushed down suture leg 56. Then suture leg 56 is captured and a fourth interim (underhand) half-hitch knot is formed and pushed down leg 50. Finally, a fifth interim (overhand) half-hitch knot is formed in leg 50 and pushed down leg 56. This series of interim knots creates a secure and proven Revo® knot to approximate tissue to bone. (The Revo® knot technique is described with text and graphics in the Super Revo® surgical technique, document # CST 3018 incorporated by reference herein and available from Linvatec Corporation, 11311 Concept Boulevard, Largo, Fla. 33773.)

As previously mentioned, the various motions of elongated components 12 and 14 may be effected by moving them individually and manually to the various positions described above or these components may be manipulated via handles and other structures situated at their proximal ends. For example, outer tubular member 12 may be attached to a cam system operated by a pistol grip type of handle while inner member 14 may be attached to a trigger mechanism. A device suitable for adaptation to such an embodiment is shown in U.S. Pat. No. 6,074,395 (Trott et al.) assigned to the assignee hereof and incorporated by reference herein. Squeezing the trigger mechanism may automatically push member 14 from outer member either all at once or in stages. Thus, for example, one trigger pull could move inner member 14 from the position shown in FIG. 4 to the position shown in FIG. 5. A second trigger pull could then be used to move the inner member 14 from the position shown in FIG. 5 to the position shown in FIG. 6. A third trigger pull could then be used to deploy the fingers outside of the outer tubular member 12 to the position shown in FIG. 7. A final trigger pull could be used to retract the fingers.

If one desired to equip knot tier 10 with a mechanism to select the degree of rotation of the inner member and/or alternately the degree turn for each successive loop, such a device could be made by providing, for example, suitable cam tracks or similar designs. Thus, a surgeon could form a knot with the first loop turned through 270°, a second loop turned through 540° and a third loop turned through 360°, all without removing knot tier 10 from the work site.

It will be understood by those skilled in the art that numerous improvements and modifications may be made to the preferred embodiment of the invention disclosed herein without departing from the spirit and scope thereof.

What is claimed is:

1. A knot tier for tying a knot in suture comprising:
   an elongated tubular member having a cylindrical wall, a proximal end and a distal end, said cylindrical wall provided, at a predetermined point adjacent said distal end, with a transverse slot for receiving a length of suture therein and positioning it transversely within the interior of said tubular member;
   an elongated manipulating member having a proximal end and a distal end and situated coaxially and slidably within said tubular member, said manipulating member movable between a first, proximal-most position in which it is retracted within said tubular member with its distal-most end situated proximal to said predetermined point, and a second, distal-most position in which it is extended distally from said tubular member, said manipulating member comprising a pair of diametrically opposed finger members situated at the distal end of said manipulating member, said finger members adapted to be slidable and rotatable within said tubular member and to be placed into a first orientation in which they are spaced apart a first predetermined distance sufficient to enable them to fit within said tubular member when said manipulating member is at said first, proximal-most position and further adapted to be placed into a second orientation in which they are spaced apart a second predetermined distance when said manipulating member is at said second, distal-most position extended distally from said distal end of said tubular member;
   a distally facing suture receiving channel situated at the distal end of each finger member;
   linear moving means for moving said pair of finger members distally and extending them a predetermined distance beyond the distal end of said tubular member; and
   rotating means for rotating said pair of finger members a predetermined amount.

2. A knot tier according to claim 1 further comprising:
   a helical track means on one of said manipulating member or tubular member and a cooperating track engaging element on the other of said manipulating member or tubular member to cause said linear means and said rotating means to operate simultaneously to rotate said finger members while they are being moved distally relative to said tubular member.

3. A knot tier according to claim 1 wherein said predetermined amount is sufficient to form a loop in a length of suture received in said suture receiving channels.

4. A knot tier according to claim 1 wherein said transverse slot is inclined so that its radially innermost ends are situated distally of its radially outermost end.

5. A knot tier according to claim 1 wherein said finger members are biased to automatically conform to said second orientation when they extend said predetermined distance beyond said distal end of said tubular member.

6. A knot tier according to claim 1 wherein said finger members further comprise a longitudinal channel communicating with and extending proximally from each suture receiving channel.

7. A knot tier according to claim 2 further comprising:
   a radially extending cam pin provided on one of said manipulating member or tubular member, said cam pin slidably received within a helically, longitudinally extending cam track situated on an adjacent surface of the other of said manipulating member or tubular member.

8. A knot tier according to claim 2 wherein said rotating means rotates said finger members 270° as said manipulating member is moved from said first proximal-most position to said second distal-most position.

9. A knot tier according to claim 1 further comprising:
   a longitudinal slot extending between said transverse slot and said distal end of said tubular member; and
   distally facing suture receiving notch at the distal end of said tubular member, said notch adapted to enable said tubular member to slidably engage the suture to push a knot distally.

10. A knot tier according to claim 1 further comprising:
    a distally facing projection at said distal end of said tubular member for separating adjacent suture legs.

11. A knot tier according to claim 10 further comprising:
    a distally inclined surface for guiding a suture leg separated by said distally facing projection onto the outer surface of said tubular member.

12. A method for tying a knot in a suture, the suture having two legs extending from a site at which the knot is to be tied, the method comprising the steps of:
    providing a knot tier comprising:
       an elongated tubular member having a cylindrical wall, a proximal end and a distal end, said cylindrical wall provided, at a predetermined point adjacent said distal end, with a transverse slot for receiving a length of suture therein and positioning it transversely within the interior of said tubular member;
       an elongated manipulating member having a proximal end and a distal end and situated coaxially and slidably within said tubular member, said manipulating member movable between a first, proximal-most position in which it is retracted within said tubular member with its distal-most end situated proximal to said predetermined point, and a second, distal-most position in which it is extended distally from said tubular member, said manipulating member comprising a pair of diametrically opposed finger members situated at the distal end of said manipulating member, said finger members adapted to be slidable and rotatable within said tubular member and to be placed into a first orientation in which they are spaced apart a first predetermined distance sufficient to enable them to fit within said tubular member when said manipulating member is at said first, proximal-most position and further adapted to be placed into a second orientation in which they are spaced apart a second predetermined distance when said manipulating member is at said second, distal-most position extended distally from distal end of said tubular member;

a distally facing suture receiving (engaging) channel situated at the distal end of each finger member;

linear moving means for moving said pair of finger members distally and extending them a predetermined distance beyond the distal end of said tubular member;

rotating means for rotating said pair of finger members a predetermined amount;

retracting said manipulating member proximally of said predetermined point;

engaging one leg of the suture in said transverse slot to position it within said tubular member;

engaging the suture within the tubular member within said suture receiving channels;

extending said diametrically opposed finger members from the tubular member;

rotating said diametrically opposed finger members to form a loop in said suture;

passing the other leg of said suture through said loop;

retracting the finger members to thereby form a knot; and disengaging said suture from said transverse slot.

13. A method according to claim 12 wherein said step of rotating said diametrically opposed finger members further comprises the step of rotating them more than 180°.

14. A method according to claim 12 wherein said steps of extending and rotating are done simultaneously.

15. A method according to claim 12 wherein said knot tier further comprises a longitudinal slot extending between said transverse slot and said distal end of said tubular member, and a distally facing suture receiving notch at the distal end of said tubular member, said notch adapted to enable said tubular member to slidably engage the suture to push a knot distally, and said method further comprises the steps of:

disengaging said suture from only a portion of said transverse slot;

engaging said suture with said notch at a point adjacent said notch;

pushing said knot distally with said notch; and disengaging the remaining portion of said suture from said tubular member.

* * * * *